United States Patent
Heo et al.

(10) Patent No.: US 9,398,674 B2
(45) Date of Patent: Jul. 19, 2016

(54) X-RAY IMAGE APPARATUS

(71) Applicant: SAMSUNG ELECTRONICS CO., LTD., Suwon-si (KR)

(72) Inventors: Min Ho Heo, Suwon-si (KR); Seok Mo Ko, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 192 days.

(21) Appl. No.: 14/160,975

(22) Filed: Jan. 22, 2014

(65) Prior Publication Data

US 2014/0205064 A1 Jul. 24, 2014

(30) Foreign Application Priority Data

Jan. 21, 2013 (KR) .................. 10-2013-0006610

(51) Int. Cl.
*H05G 1/02* (2006.01)
*A61B 6/00* (2006.01)

(52) U.S. Cl.
CPC .............. *H05G 1/02* (2013.01); *A61B 6/4429* (2013.01); *A61B 6/4464* (2013.01)

(58) Field of Classification Search
None
See application file for complete search history.

(56) References Cited

U.S. PATENT DOCUMENTS

| | | | | |
|---|---|---|---|---|
| 3,891,856 A * | 6/1975 | Amor, Jr. | ............ | A61B 6/4464 378/117 |
| 3,934,140 A * | 1/1976 | Dutertre | ............ | A61B 6/04 378/179 |
| 4,104,527 A * | 8/1978 | Tomita | ............ | A61B 6/035 378/11 |
| 4,340,971 A * | 7/1982 | Furuichi | ............ | H02P 5/50 378/40 |
| 4,387,468 A * | 6/1983 | Fenne | ............ | A61B 6/447 378/198 |
| 5,235,344 A * | 8/1993 | Shinkawa | ............ | H01Q 1/103 318/603 |
| 5,793,837 A * | 8/1998 | Mezhinsky | ............ | A61B 6/14 378/38 |
| 2006/0184124 A1 * | 8/2006 | Cowan | ............ | A61M 5/007 604/155 |
| 2009/0129553 A1 * | 5/2009 | Halsmer | ............ | G03B 42/02 378/167 |
| 2013/0240353 A1 * | 9/2013 | Watanabe | ............ | H01J 37/20 204/298.36 |

FOREIGN PATENT DOCUMENTS

CH    EP 0053579 A1 *  6/1982   ........... A61B 6/4429
EP    0 053 579 A1    6/1982

(Continued)

OTHER PUBLICATIONS

European Search Report dated Jun. 10, 2014 in corresponding European Patent Application 14151840.7.

*Primary Examiner* — Andrew Smyth
(74) *Attorney, Agent, or Firm* — Staas & Halsey LLP

(57) ABSTRACT

Disclosed herein is an X-ray image apparatus having an improved rotating unit for preventing a blind spot in which an X-ray-generating unit is not rotated from being generated. The X-ray image apparatus includes an X-ray-generating unit configured to generate X-rays and radiate the X-rays, an X-ray-detecting unit configured to detect the X-rays radiated from the X-ray-generating unit, and a rotating unit configured to rotate the X-ray-generating unit. Here, the rotating unit includes a rotating frame coupled to one side of the X-ray-generating unit; a protrusion configured to protrude from one side of the rotating unit; and a stopper being in contact with the protrusion to halt a rotation of the rotating frame and being provided such that the stopper can be moved in a preset zone. Since the stopper securing the rotating frame of the rotating unit can be moved in the preset zone, it is possible to prevent a blind spot caused by a restriction of the rotation of the rotating frame from being generated.

21 Claims, 11 Drawing Sheets

(56) References Cited

FOREIGN PATENT DOCUMENTS

| EP | 0053579 | B1 | * | 10/1985 | ............ | A61B 6/4429 |
| EP | 1 434 076 | A1 | | 6/2004 | | |
| JP | EP 1434076 | A1 | * | 6/2004 | ............. | F16M 11/06 |
| JP | EP 1434076 | B1 | * | 1/2007 | ............. | F16M 11/06 |

* cited by examiner

X-RAY IMAGE APPARATUS

CROSS-REFERENCE TO RELATED APPLICATIONS

This application claims the benefit of Korean Patent Application No. 10-2013-0006610, filed on Jan. 21, 2013 in the Korean Intellectual Property Office, the disclosure of which is incorporated herein by reference.

BACKGROUND

1. Field

One or more embodiments of the present disclosure relate to an X-ray image apparatus, and more particularly, to an X-ray image apparatus having an improved rotating unit for preventing the generation of a blind spot in which an X-ray-generating unit is not rotated.

2. Description of the Related Art

An X-ray image apparatus which has been generally employed for medical purposes is an apparatus that uses X-rays to acquire an interior image of the human body. The X-ray image apparatus is utilized for inspecting injuries or diseases that occur inside human body. Such diseases are often invisible to the naked eye.

The X-ray image apparatus can acquire an image of the inside of the human body through a method of radiating X-rays to a photographing site such as a head, chest, and the like and detecting the penetrated X-rays.

The X-ray image apparatus is equipped with an X-ray tube radiating X-rays to a photographing site, a high-voltage generator generating high-voltage required for generating X-rays, and equipment such as a moving device for moving a radiation location and a direction of the X-rays. In addition, the X-ray image apparatus is equipped with an operating device provided for enabling an operator to control the apparatus.

The X-ray image apparatus further includes an X-ray-detecting unit receiving the irradiated X-rays, converting the received X-rays into a digital signal, and transmitting the digital data to a personal computer. The X-ray-detecting unit may be installed on a table for a patient, so that X-ray photography is performed while a patient is standing on the table. In some apparatusses, the X-ray-detecting unit is secured. However, nowadays an attachable/detachable X-ray-detecting unit is manufactured and can be simultaneously utilized on a stand or on a table for a patient.

The X-ray image apparatus may include a rotating unit for rotating at least one of the X-ray-generating unit and the X-ray-detecting unit. By a rotation of the rotating unit, the X-ray-generating unit or the X-ray-detecting unit can be rotated with respect to a Z-axis.

In a conventional apparatus, the rotating unit cannot be completely rotated, thus when the X-ray-generating unit or the X-ray-detecting unit is rotated, a blind spot is generated. In this case, a user should move the X-ray-generating unit or the X-ray-detecting unit.

SUMMARY

Additional aspects and/or advantages will be set forth in part in the description which follows and, in part, will be apparent from the description, or may be learned by practice of the disclosure.

Therefore, it is an aspect of the present disclosure to provide a rotating unit which can rotate at least one of an X-ray-generating unit and an X-ray-detecting unit to prevent a blind spot from being generated.

It is an aspect of the present disclosure to provide an X-ray image apparatus including an X-ray-generating unit configured to generate X-rays and radiate the X-rays; an X-ray-detecting unit configured to detect the X-rays radiated from the X-ray-generating unit; and a rotating unit configured to rotate the X-ray-generating unit. Here, the rotating unit includes a rotating frame coupled to one side of the X-ray-generating unit; a protrusion configured to protrude from one side of the rotating unit; and a stopper being in contact with the protrusion to halt a rotation of the rotating frame and being provided such that the stopper can be moved in a preset zone.

One side of the stopper may be coupled to a driving unit for moving the stopper, the stopper may be moved in the first direction when the rotating frame is rotated in a counterclockwise direction, and the stopper may be moved in the second direction when the rotating frame is rotated in a clockwise direction.

The driving unit may include one or more elastic members, and the stopper may be moved in the preset zone by the elastic force of the elastic member.

The X-ray image apparatus may further include a housing to which at least one elastic member is coupled, the housing being configured to receive one side of the stopper.

The at least one elastic member may include a first elastic member coupled to one side of the housing and a second elastic member coupled to the other side of the housing.

The X-ray image apparatus may further include a bracket to which the housing is coupled, and which includes a groove for guiding a movement of the elastic member.

The driving unit may include one or more gears.

The X-ray image apparatus may further include a housing coupled to the stopper via one side thereof and coupled to the gear via the other side thereof.

The X-ray image apparatus may further include a shaft coupled to the gear via one side thereof and coupled to the housing via the other side thereof.

The shaft may have a thread portion provided on at least a portion thereof, and the stopper may be moved along the thread portion.

The driving unit may further include a power-generating device.

The X-ray image apparatus may further include a buffer part coupled to the stopper for preventing generation of a noise or damage caused when the stopper is in contact with the protrusion.

It is another aspect of the present disclosure to provide an X-ray image apparatus including an X-ray-generating unit configured to generate X-rays and radiate the X-rays; an X-ray-detecting unit configured to detect the X-rays radiated from the X-ray-generating unit; and a rotating unit configured to rotate at least one of the X-ray-generating unit and the X-ray detecting unit. Here, the rotating unit includes a rotating frame coupled to one side of at least one of the X-ray-generating unit and the X-ray detecting unit; a stopper being in contact with one side of the rotating frame to halt a rotation of the rotating frame; and a driving unit for moving the stopper from a first point to a second point or from the second point to the first point.

The X-ray image apparatus may further include a protrusion protruding from one side of the rotating frame to allow the stopper to be in contact with the protrusion.

The stopper may include a head part and a body part extending from the head part, and the head part may be in contact with the protrusion.

The driving unit may include at least one elastic member, and the stopper may be moved from the first point to the second point by a linear movement of the elastic member.

The elastic member may include a first elastic member being compressed when the stopper is moved to the second point and a second elastic member being compressed when the stopper is moved to the first point.

The stopper may further include a bracket provided for preventing the stopper from being deviated from a zone between the first point and the second point and a housing coupled to the bracket via one surface thereof and coupled to the stopper through the other surface thereof.

The driving unit may include at least one gear, and the stopper may be moved from the first point to the second point by a rotational movement of the gear.

The at least one gear may include a first gear rotated according to a rotation of the rotating frame and a second gear determining a location of the stopper according to a rotation of the first gear.

It is another aspect of the present disclosure to provide a rotating unit configured to rotate an X-ray apparatus including one of an X-ray-generating unit and an X-ray-detecting unit. The rotating unit includes a rotating frame coupled to the X-ray apparatus, a protrusion configured to protrude from the rotating unit, and an adjustable stopper configured to make contact with the protrusion to halt a rotation of the rotating frame.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
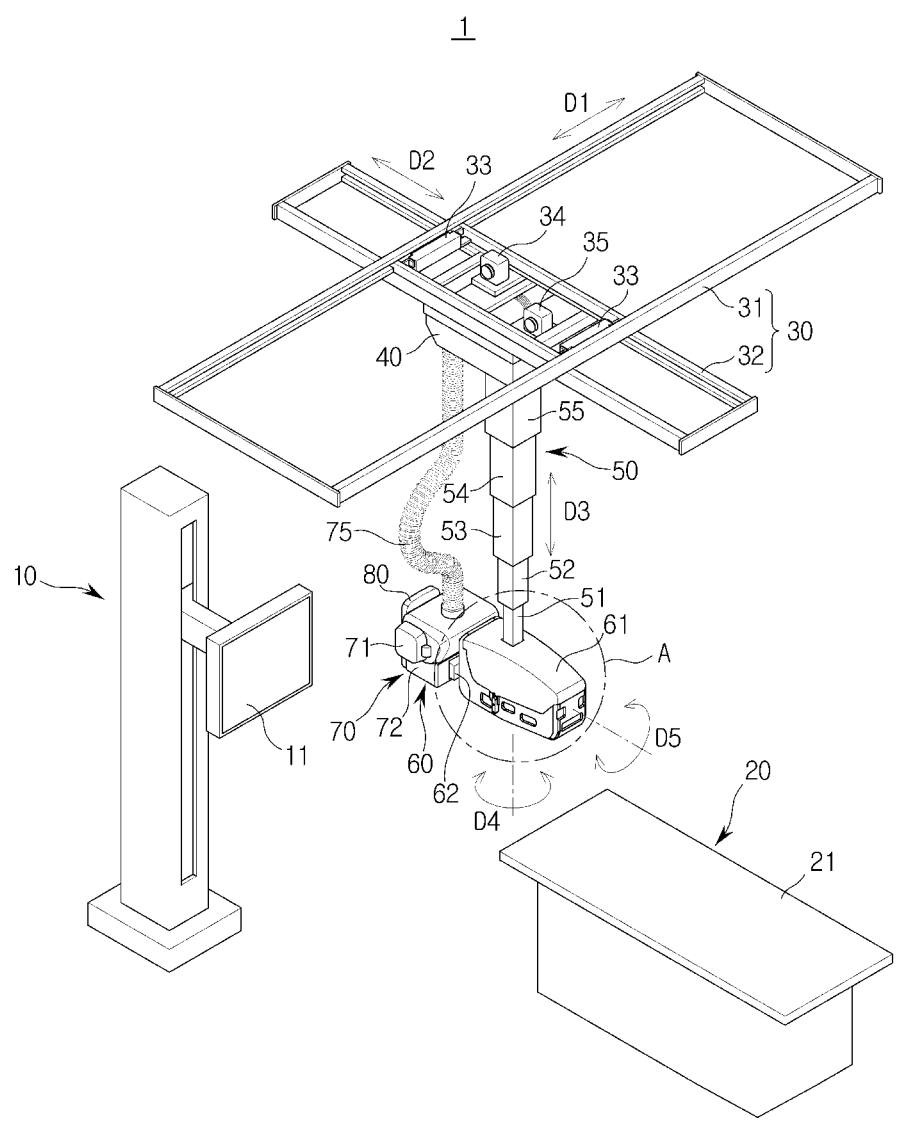
FIG. 1 is a view illustrating an essential structure of an X-ray image apparatus according to one embodiment of the present disclosure.

Reference will now be made in detail to the embodiments of the present disclosure, examples of which are illustrated in the accompanying drawings, wherein like reference numerals refer to like elements throughout. An X-ray image apparatus according to the spirit of the present disclosure can be applicable to a various kinds of X-ray image apparatuses. Hereinafter, however, a ceiling type X-ray image apparatus having a guide rail to be installed on a ceiling of an inspection room is illustrated.

Figure 2:
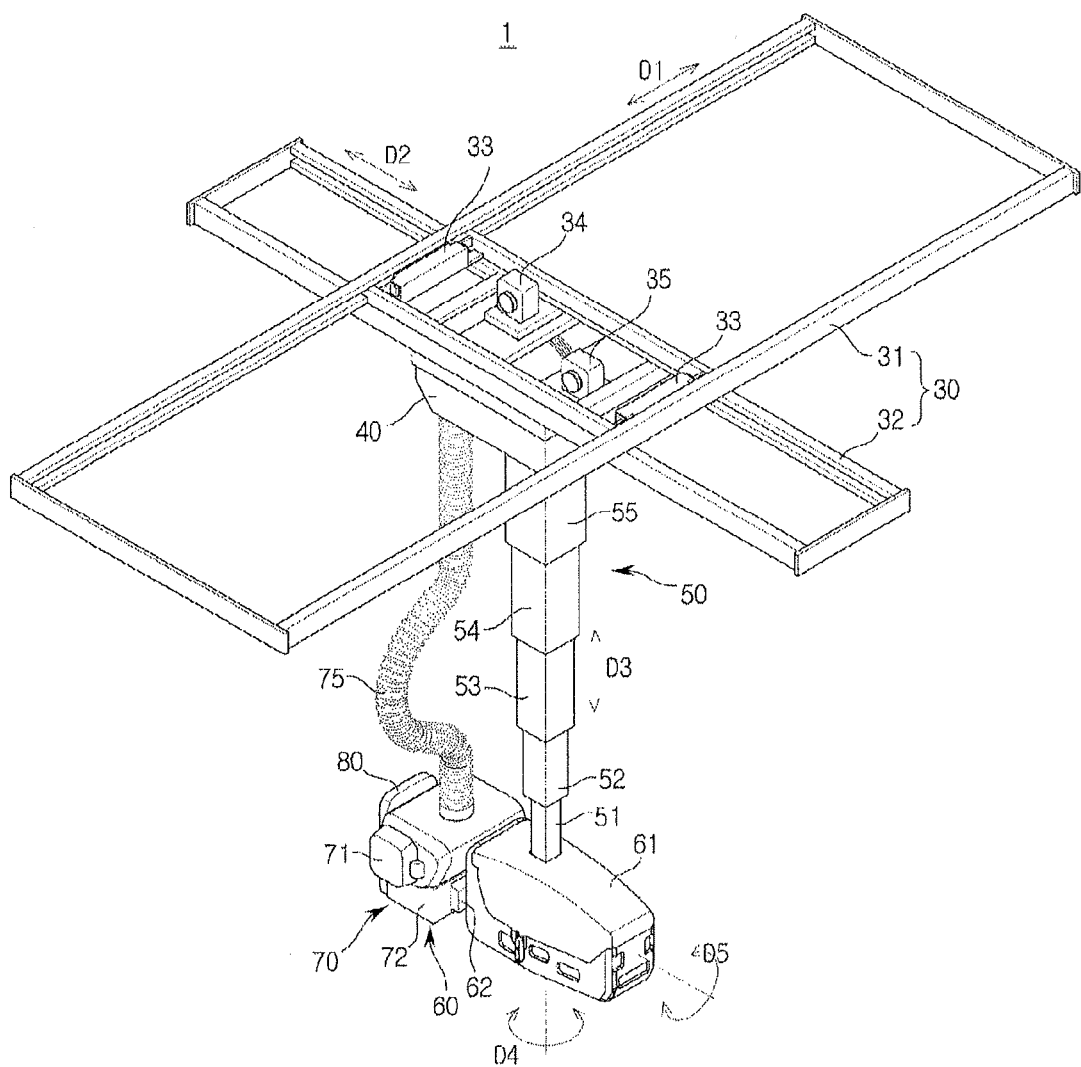
FIG. 2 is a view illustrating an X-ray-generating unit and a rail structure according to one embodiment of the present disclosure.

FIG. 1 is a view illustrating a structure of an X-ray image apparatus according to one embodiment of the present disclosure, and FIG. 2 is a view illustrating an X-ray-generating unit and a rail structure according to an embodiment of the present disclosure.

As shown in FIG. 1 and FIG. 2, an X-ray image apparatus 1 is equipped with a guide rail 30, a moving carriage 40, a control unit (not shown) provided in the moving carriage 40, a post frame 50, driving units 33, 34, and 35, an X-ray-generating unit 70, a measuring unit (not shown), and an operating unit (not shown).

The X-ray image apparatus 1 may be further equipped with a photographing stand 10 and a photographing table 20, and the photographing stand is provided with an X-ray-detecting unit detecting X-rays penetrating the object.

The guide rail 30, the moving carriage 40, and the post frame 50 are provided for moving the X-ray-generating unit 70 toward an object.

The guide rail 30 includes a first guide rail 31 and a second guide rail 32 which are installed such that the first guide rail and the second guide rail form a certain angle. The first guide rail 31 and the second guide rail 32 can be extended in directions perpendicular to each other.

The first guide rail 31 is provided on a ceiling of an inspection room in which the X-ray image apparatus 1 is arranged. The second guide rail 32 is placed below the first guide rail 31 and is slidably mounted to the first guide rail 31. A roller (not shown) may be installed on the first guide rail 31 and moved along the first guide rail 31. The second guide rail 32 is connected to the roller (not shown), so that the second guide rail 32 can be moved along the first guide rail 31.

The direction in which the first guide rail 31 is extended is defined as a first direction D1, and the direction in which the second guide rail 32 is extended is defined as a second direction D2. Thus, the first direction D1 and the second direction D2 may be perpendicular to each other and may be parallel with the ceiling of the inspection room.

The moving carriage 40 is disposed under the second guide rail 32 to allow the moving carriage to be moved along the second guide rail 32. A roller (not shown) may be installed on the moving carriage 40 for enabling the moving carriage to be moved along the second guide rail 32. Thus, the moving carriage 40 can be moved in the first direction D1 together with the second guide rail 32 and can be moved in the second direction D2 along the second guide rail 32. The control unit (not shown), which controls driving of the driving units 33, 34, and 35 according to the measuring result of the measuring unit (not shown), may be provided in the moving carriage 40.

The post frame 50 is fixed to the moving carriage 40 and placed under the moving carriage 40. The post frame 50 may be provided with a plurality of posts 51, 52, 54, 54, and 55.

The plurality of posts 51, 52, 54, 54, and 55 are telescopically connected to each other, so that a length of the post frame 50 can be increased or decreased in an upward direction and a downward direction of the inspection room while the post frame 50 is secured to the moving carriage 40.

The direction in which the length of the post frame 50 is increased or decreased is defined as a third direction D3. Thus, the third direction D3 may be orthgonal to each of the first direction D1 and the second direction D2.

The X-ray-generating unit 70 is a device for radiating the X-rays to the object.

The X-ray-generating unit 70 may be equipped with an X-ray tube 71 generating the X-rays and a collimator 72 for guiding the generated X-rays toward the object.

A swivel joint 60 is disposed between the X-ray-generating unit 70 and the post frame 50.

The swivel joint 60 couples the X-ray-generating unit 70 with the post frame 50 and supports a load applied to the X-ray-generating unit 70. The swivel joint 60 may include a rotating unit 100 for rotating the X-ray-generating unit 70. The rotating unit is illustrated later.

The swivel joint 60 may have a first swivel joint 61 connected to the lowest post 51 of the post frame 50 and a second swivel joint 62 connected to the X-ray-generating unit 70.

The first swivel joint 61 is provided such that the first swivel joint can be rotated with respect to a central axis of the post frame 50 extending in the vertical direction of the inspection room. Thus, the first swivel joint 61 can be rotated in a plane perpendicular to the third direction D3. At this time, a rotational direction of the first swivel joint 61 can be newly defined. A newly defined fourth direction D4 is a rotational direction of an axis which is parallel with the third direction D3.

The second swivel joint 62 is provided such that the second swivel joint can be rotated on a plane which is perpendicular to the ceiling of the inspection room. Thus, the second swivel joint 62 can be rotated in the rotational direction of an axis which is parallel with the first direction D1 or the second direction D2. At this time, a rotational direction of the second swivel joint 62 can be newly defined. A newly defined fifth direction D5 is a rotational direction of an axis which is extended in the first direction D1 or the second direction D2.

The X-ray-generating unit 70 is connected to the swivel joint 60, so that the X-ray-generating unit can be rotationally moved in the fourth direction D4 and the fifth direction D5. In addition, the X-ray-generating unit 70 is connected to the post frame 50 through the swivel joint 60, so that the X-ray-generating unit can be linearly moved in the first direction D1, the second direction D2, and the third direction D3.

The driving units 33, 34, and 35 are provided for moving the X-ray-generating unit 70 in the first direction D1 to the fifth direction D5. A motor which is electrically driven may be utilized as the driving units 33, 34, and 35.

A plurality of driving units 33, 34, and 35 may be provided such that each driving unit corresponds to each direction.

In view of convenience of a design, each of the driving units 33, 34, and 35 may be disposed at various locations. For example, the first driving unit 33 for moving the second guide rail 32 in the first direction D1 is disposed around the first guide rail 31, the second driving unit 34 for moving the moving carriage 40 in the second direction D2 is disposed around the second guide rail 32, and the third driving unit (not shown) for increasing or decreasing a length of the post frame 50 in the third direction D3 may be disposed in the moving carriage 40. In addition, the fourth driving unit (not shown) for rotationally moving the X-ray-generating unit 70 in the fourth direction D4 is disposed around the first swivel joint 61, and the fifth driving unit (not shown) for rotationally moving the X-ray-generating unit 70 in the fifth direction D5 is disposed around the second swivel joint 62.

Each of the driving units 33, 34, and 35 may be connected to a power transmitting unit (not shown) to linearly or rotationally move the X-ray-generating unit 70 in the first to fifth directions D1 to D5. A belt and pulley, a chain and sprocket and a shaft, which have been generally utilized, may be employed as the power transmitting unit (not shown).

An operating unit 80 is provided on one side of the X-ray-generating unit 70, and this operating unit provides an interface that can input various kinds of information about the X-ray photography and can operate each unit of the equipment.

The operating unit 80 may include a display part (not shown) on which the interface is capable of inputting various kinds of information about the X-ray photography and is capable of operating each unit of the equipment. A handle (not shown) is provided to enable a user to grasp the operating unit 80. In addition, buttons (not shown) for operating each unit of the equipment may be provided on the operating unit. A user can grasp the handle (not shown) of the operating unit 80 and apply force or torque to move the X-ray-generating unit 70.

The control unit (not shown) may be electrically connected to the equipment including the driving units 33, 34, 35 and the operating unit 80 provided in the X-ray image apparatus 1 and can control the equipment. The control unit (not shown) can be provided in the moving carriage 40.

In addition, the X-ray image apparatus 1 may be provided with the measuring unit (not shown) for measuring a force or a torque exerted by a user to grasp the user's intention with respect to moving the X-ray-generating unit or the X-ray-detecting unit. In order for the control unit (not shown) to operate the driving units 33, 34, and 35 in response to a force or a magnitude measured in the measuring unit (not shown), a signal measured in the measuring unit (not shown) is transmitted to the control unit (not shown).

Figure 3:
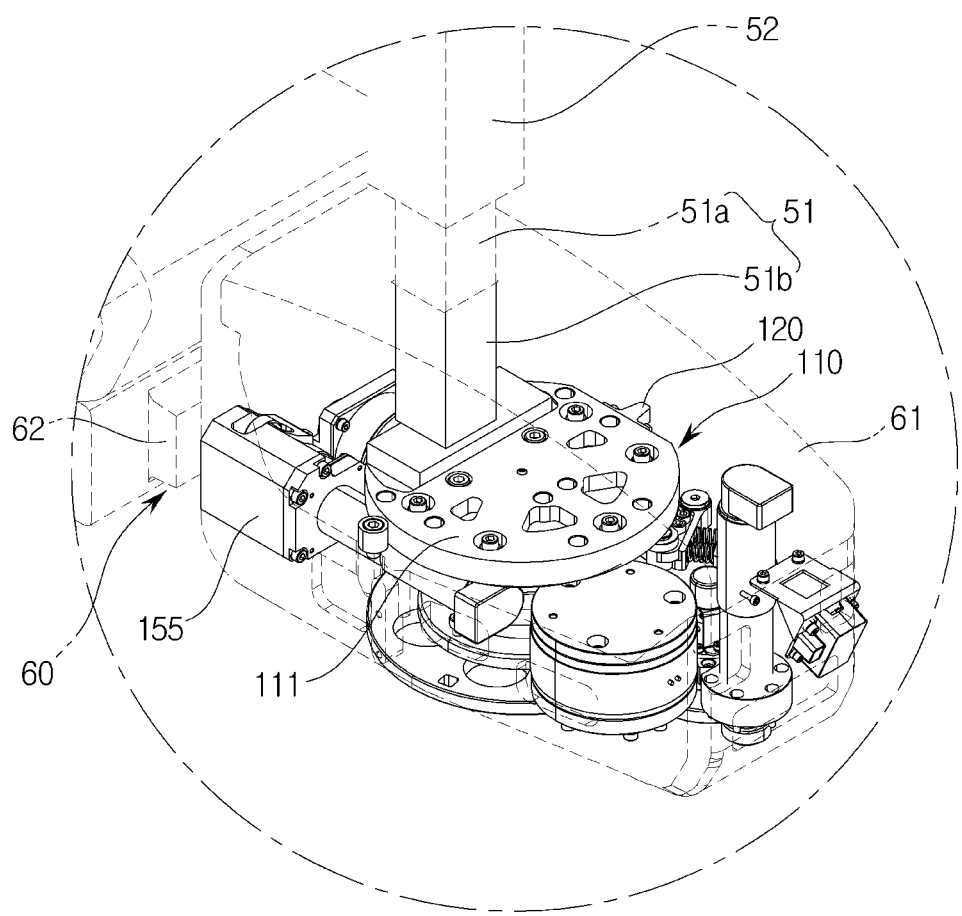
FIG. 3 is a perspective view illustrating the interior of A of FIG. 1.
Figure 4:
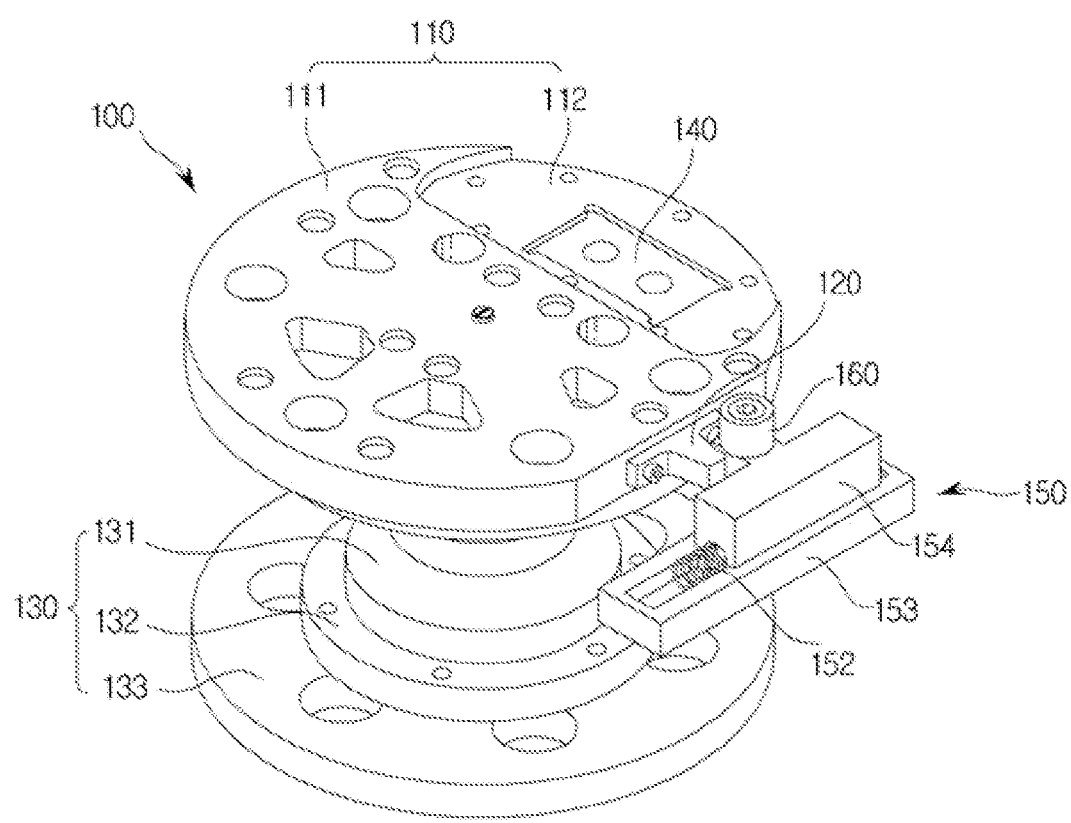
FIG. 4 is a perspective view illustrating a rotating unit according to one embodiment of the present disclosure.
Figure 5:
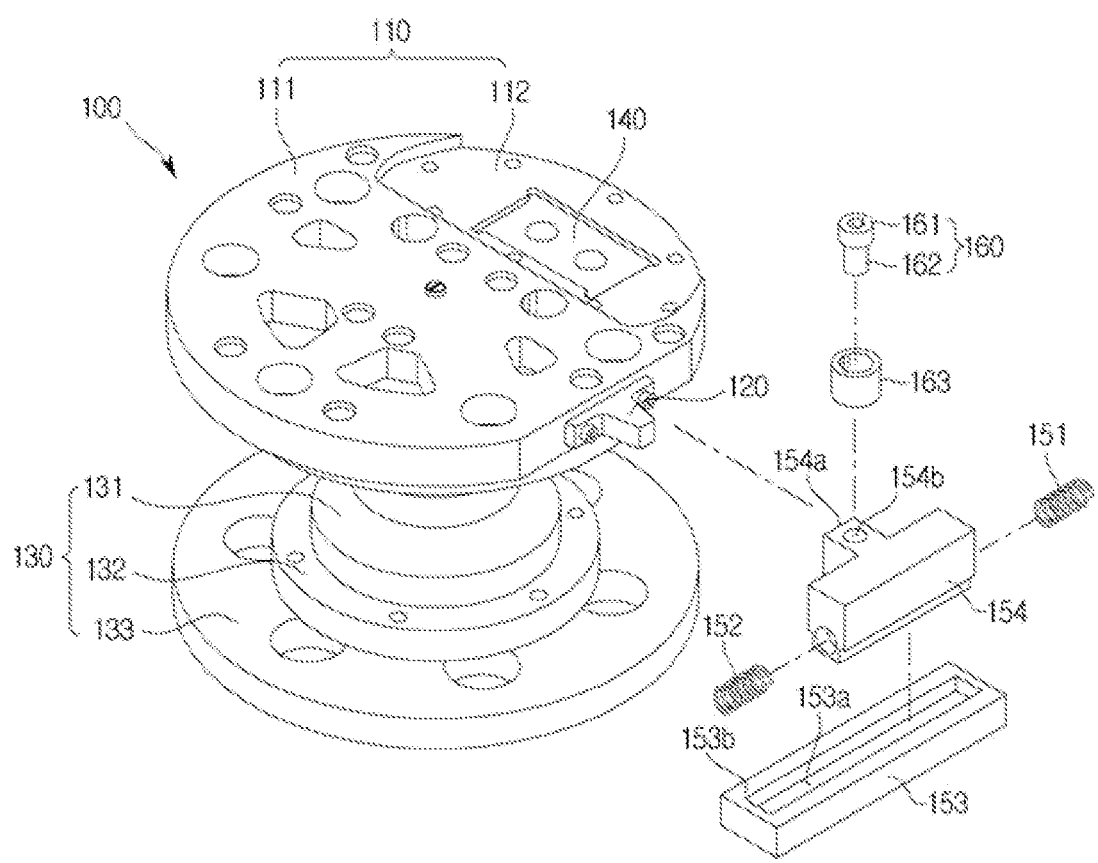
FIG. 5 is an exploded perspective view of a rotating unit according to one embodiment of the present disclosure.

FIG. 3 is a perspective view illustrating the interior of A of FIG. 1, FIG. 4 is a perspective view illustrating the rotating unit according to one embodiment of the present disclosure, and FIG. 5 is an exploded perspective view of the rotating unit according to one embodiment of the present disclosure.

One embodiment shown in FIG. 3, FIG. 4 and FIG. 5 illustrates the rotating unit 100 placed in the first swivel joint 61, however, the present disclosure is not limited thereto. If at least one of the X-ray-generating unit 70 and the X-ray-detecting unit is rotated, the rotating unit 100 of the present disclosure can be applied to either of the X-ray-generating unit 70 and the X-ray-detecting unit.

According to an embodiment of the present disclosure, a rotating unit 100 is provided in the first swivel joint 61.

The swivel joint 60 of the present disclosure includes the rotating unit 100 for rotating the X-ray-generating unit 70 or the X-ray-detecting unit. The rotating unit 100 includes a rotating frame 130, to which one side of the X-ray-generating unit 70 is coupled so that the X-ray-generating unit may be rotated. A fixing frame 110 can be secured to the other side of the rotating unit 100. According to the structure shown in the drawing, the fixing frame 110 is placed above the rotating unit 100, and the rotating frame 130 is placed under the rotating unit.

The fixing frame 110 may include a first fixing frame 111 and a second fixing frame 112. A height-adjusting unit 140 provided for adjusting a height of the X-ray-generating unit 70 may be coupled to one side of the second fixing frame 112. The rotating frame 130 may include a first rotating frame 131, a second rotating frame 132, and a third rotating frame 133. The X-ray-generating unit 70 may be coupled to one side of the rotating frame 130.

A rotating frame 130 is coupled to a bottom surface of the first swivel joint 61, and a fixing frame 110 is provided at an upper side of the first swivel joint 61. In addition, a post frame 50 is coupled to a height-adjusting unit 140. According to an embodiment of the present disclosure, the post 51 provided at the lowest position among the plurality of posts 51, 52, 53 and 54 includes an inner post 51b disposed at an inner side of the first swivel joint 61 and an outer post 51a disposed at an outer side of the first swivel joint 61.

The rotating unit 100 may include a protrusion 120 protruding from one side of the rotating unit 100. The protrusion 120 makes contact with a stopper 160, which is described later, to enable a rotation of the rotating unit 100 to be halted.

The protrusion 120 may be provided such that the protrusion protrudes from one side of the fixing frame 110 toward an outside of the fixing frame 110.

The stopper 160 is provided for halting a rotation of the rotating frame 130 through a friction force caused when the stopper makes contact with the protrusion 120. The stopper 160 is provided such that the stopper can be moved within a preset zone. In detail, the stopper 160 can be adjusted. That is, the stopper 160 can be moved in a first direction (from a first point to a second point) and can be moved in a second direction (from the second point to the first point).

The X-ray image apparatus 1 may include a driving unit 150 for moving the stopper 160. The driving unit 150 may include a power-generating device (155) generating a power for moving the stopper 160. According to one embodiment of the present disclosure, the driving unit 150 may include one or more elastic members 151 and 152. The elastic members 151 and 152 may include a first elastic member 151 and a second elastic member 152 coupled to both sides of the stopper 160, respectively. The stopper 160 can be moved within the preset zone by elastic forces of the first elastic member 151 and the second elastic member 152, respectively. In other words, when the stopper 160 is moved in the first direction or in the second direction, at least one of the elastic members 151 and 152 may be compressed and the stopper 160 can be moved by a restoring force of the other one of the elastic members 151 and 152. The above operation will be illustrated later.

The stopper 160 may include a head part 161 and a body part 162 extending from the head part 161. The body part 162 may be coupled to a stopper-coupling part 154a provided on a housing 154. The stopper-coupling part 154a may be provided such that the stopper-coupling part protrudes in the direction of the rotating frame 110 for allowing the stopper-coupling part to easily make contact with the protrusion 120. A stopper-coupling groove 154b may be provided on at least a portion of the stopper-coupling part 154a, and the body part 162 of the stopper 160 can be inserted into the stopper-coupling groove 154b.

A buffer part 163 may be provided between the housing 154 and the stopper 160. The buffer part 163 may be coupled to the stopper 160 such that the buffer part wraps around the head part 161. The buffer part 163 may be formed of a flexible material. As one example, the buffer part 163 may be formed of a rubber-like material. Due to the flexible nature of the buffer part, it is possible to prevent generation of a noise or damage caused when the stopper 160 makes contact with the protrusion 120.

The first elastic member 151 and the second elastic member 152 may be coupled to the other side of the housing 154. The first elastic member 151 and the second elastic member 152 may be coupled to the housing to allow the stopper 160 to be located between the first elastic member 151 and the second elastic member 152.

A bracket 153 provided for guiding a movement of the stopper 160 may be coupled to a lower side of the housing 154. A groove 153a formed by grooving or denting inward the bracket may be placed on one side of the bracket 153. Deviation-preventing parts 153b are provided at both sides of the groove 153a to prevent the first elastic member 151 and the second elastic member 152 from deviating from the preset zone. The housing 154 is moved in the groove 153a according to a degree of compression of the first elastic member 151 and the second elastic member 152, so that the stopper 160 can be moved. The deviation-preventing part 153b may protrude in an upward direction of the bracket.

Figure 6:
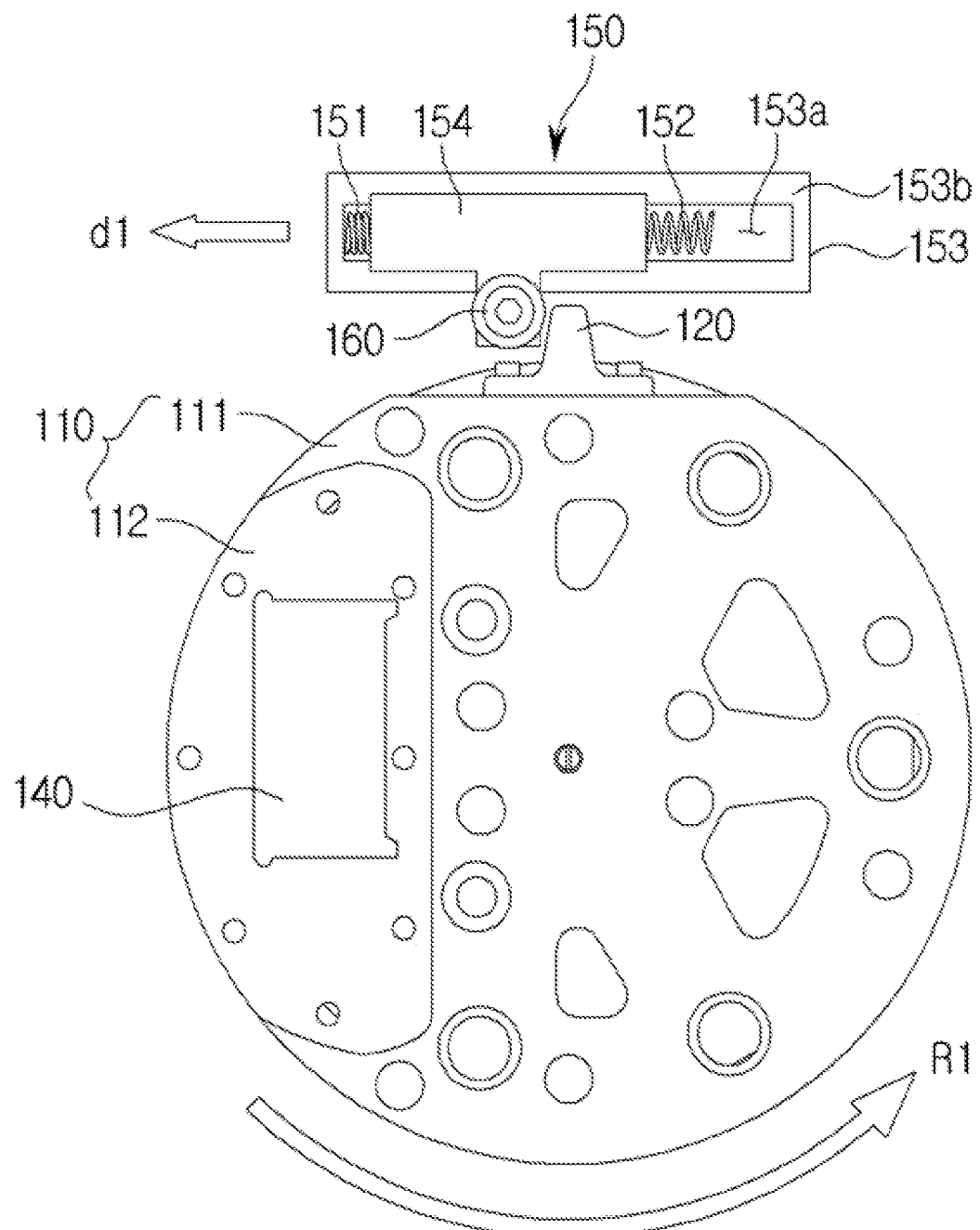
FIG. 6 and FIG. 7 are views illustrating a movement of a stopper according to a rotation of a rotating frame according to one embodiment of the present disclosure.
Figure 7:
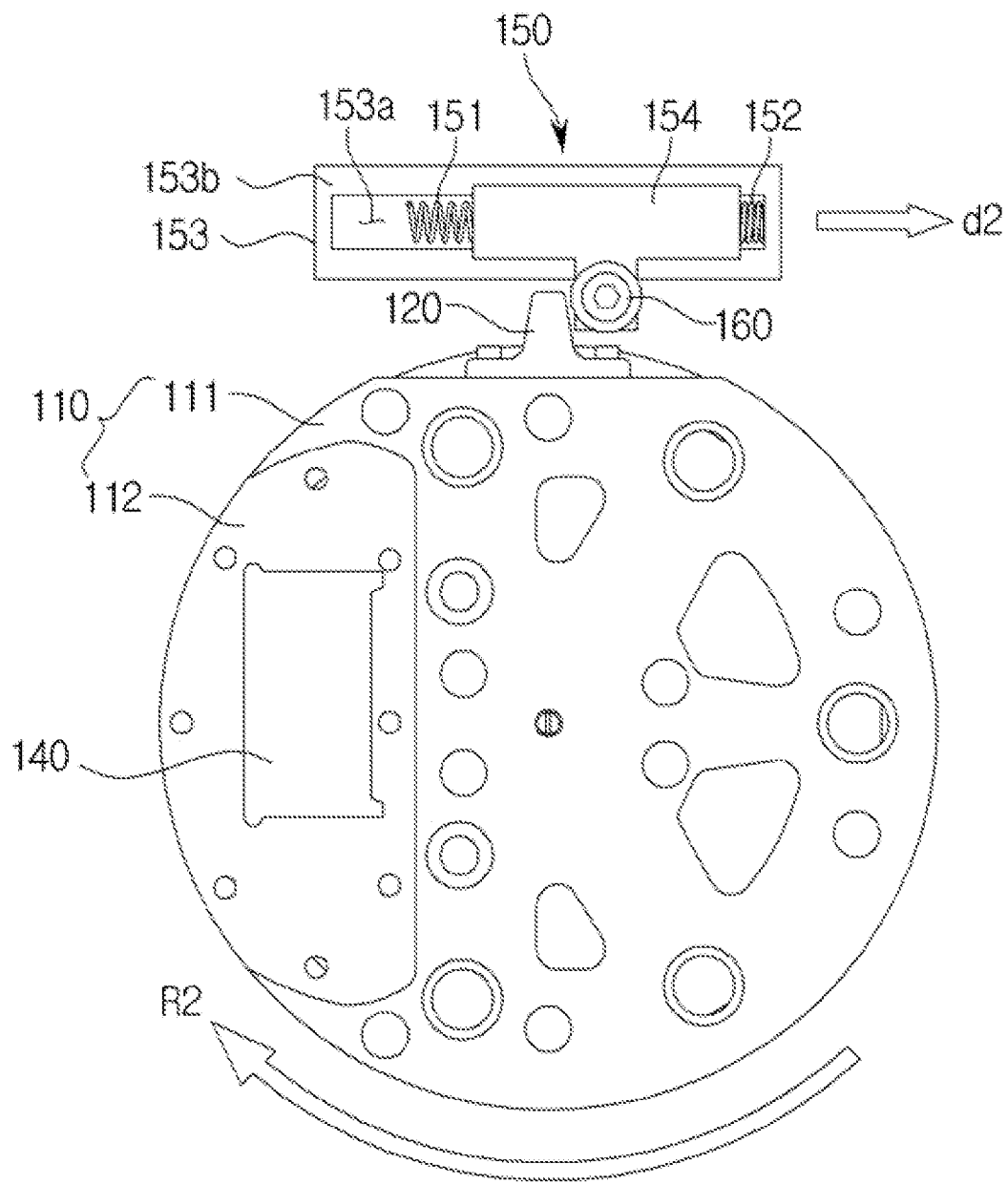

FIG. 6 and FIG. 7 are views illustrating a movement of the stopper according to a rotation of the rotating frame according to one embodiment of the present disclosure.

As shown in FIG. 6, if the rotating frame 130 is rotated in an R1 direction, which is a counterclockwise direction, the stopper 160 is moved, thereby compressing the first elastic member 151 when the stopper 160 makes contact with the protrusion 120. Due to an elastic force of the first elastic member 151, the stopper 160 may be moved up to a certain point. If the rotating frame 130 is rotated in the R1 direction, the stopper 160 is moved from the first point to the second point in the first direction d1.

As shown in FIG. 7, if the rotating frame 130 is rotated in an R2 direction, which is a clockwise direction, the stopper 160 is moved, thereby compressing the second elastic member 152 when the stopper 160 makes contact with the protrusion 120. Due to an elastic force of the second elastic member 152, the stopper 160 may be moved up to a certain point. If the rotating frame 130 is rotated in the R2 direction, the stopper 160 is moved from the second point to the first point in the second direction d2. In other words, by the linear movement of the elastic members 151 and 152, the stopper 160 can be also linearly moved from the first point to the second point or from the second point to the first point.

As illustrated above, since the stopper 160 is moved in a certain zone according to a movement of the rotating frame 130, in order for the protrusion 120 to be in contact with the stopper 160, the rotating frame 130 should be rotated 180° or more in one direction, so that it is possible to rotate 360° the X-ray-generating unit 70. Due to the above, it is possible to prevent a blind spot from being generated in which the X-ray-generating unit 70 cannot be rotated.

Figure 8:
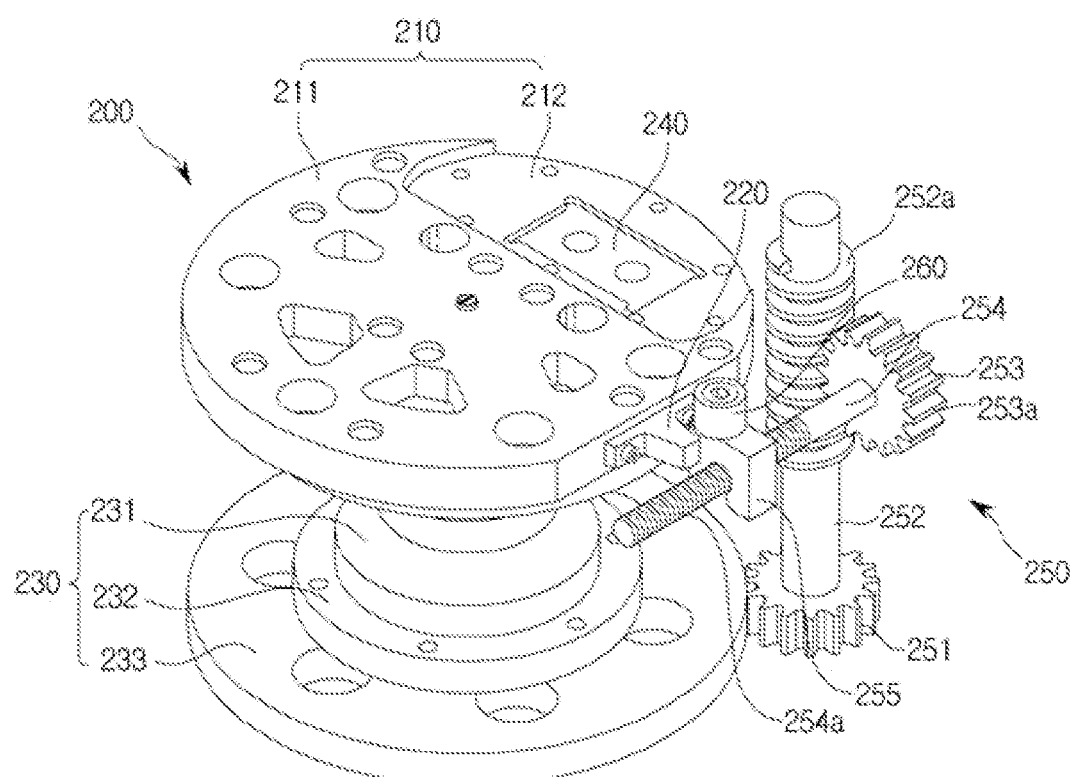
FIG. 8 is a perspective view illustrating a rotating unit according to another embodiment of the present disclosure.
Figure 9:
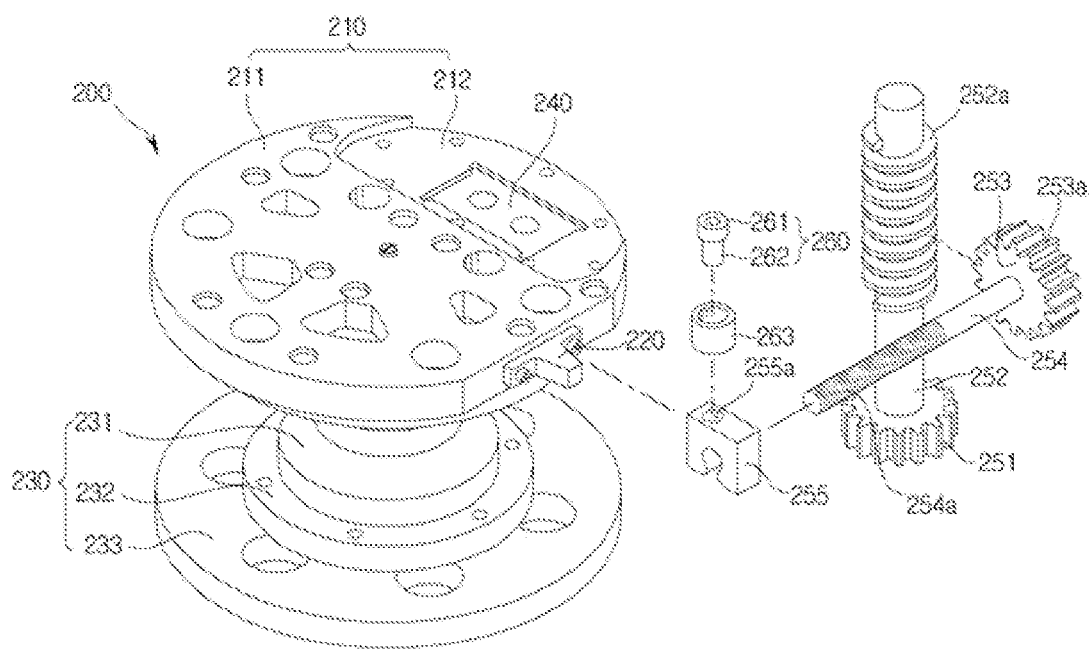
FIG. 9 is an exploded perspective view of a rotating unit according to another embodiment of the present disclosure.

FIG. 8 is a perspective view illustrating a rotating unit according to another embodiment of the present disclosure, and FIG. 9 is an exploded perspective view of the rotating unit according to another embodiment of the present disclosure.

As shown in FIG. 8 and FIG. 9, a stopper 260 can be moved by a driving unit 250 including one or more gears 251 and 253.

Similar to one or more embodiments of the present disclosure shown in FIG. 3 to FIG. 7, a rotating unit 200 of FIG. 8 and FIG. 9 may include a fixing frame 210 and a rotating frame 230. The rotating unit 200 may include a protrusion 220 protruding from one side thereof, and a rotation of the rotating frame 230 may be halted by a contact between the protrusion 220 and the stopper 260.

The driving unit 250 may include a first gear 251 which is rotated by a rotation of the rotating frame 230. In addition, the driving unit may include a second gear 253 transmitting a rotational force of the first gear 251 to the stopper 260 to allow the stopper 260 to be moved.

According to one embodiment of the present disclosure, a spur gear may be provided as the first gear 251, and a worm gear may be provided as the second gear 253. However, the present disclosure is not limited thereto. A first shaft 252 may be coupled to the first gear 251. In addition, a screw-type worm 252a is provided on at least a portion of the first shaft 252. The screw-type worm 252a and a worm wheel 253a geared with the worm and rotated constitute the second gear 253. A second shaft 254 may be coupled to the worm wheel 253a. A thread portion 254a may be formed on at least a portion of the second shaft 254. The stopper 260 may be coupled to the thread portion 254a, and the stopper 260 can be moved along the thread portion 254a according to a rotation of the second shaft 254.

The stopper 260 can be coupled to a housing 255, and the other side of the housing 255 can be coupled to the thread portion 254a. Like one or more embodiments of the present disclosure shown in FIG. 3 to FIG. 6, the stopper 260 may include a body part 262 and a head part 261, the body part 262 may be inserted into a stopper-coupling groove 255a of the housing 255, and a buffer part 263 may be provided between the stopper 260 and the housing 255.

Figure 10:
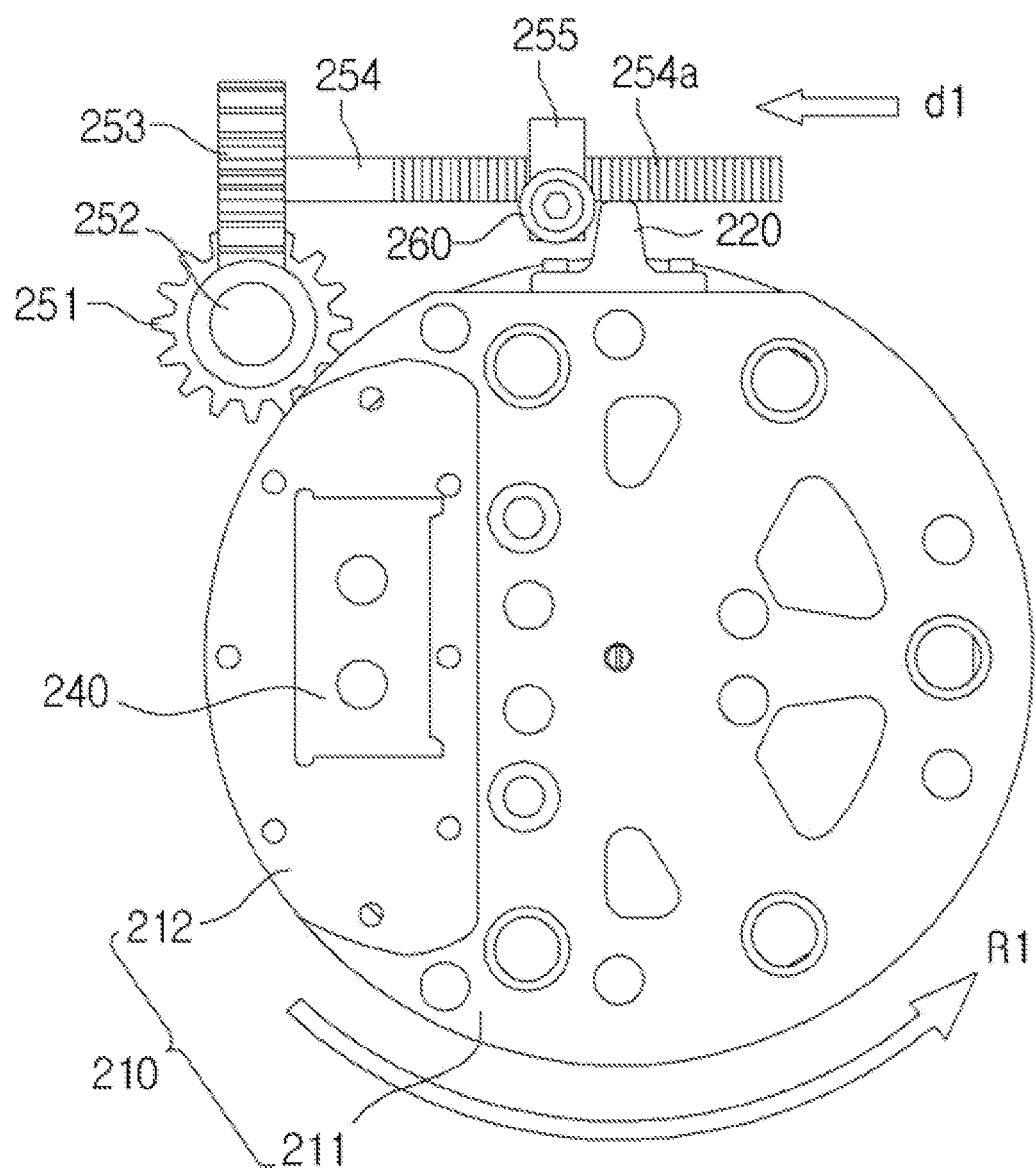
FIG. 10 and FIG. 11 are views illustrating a movement of a stopper according to a rotation of a rotating frame according to another embodiment of the present disclosure.
Figure 11:
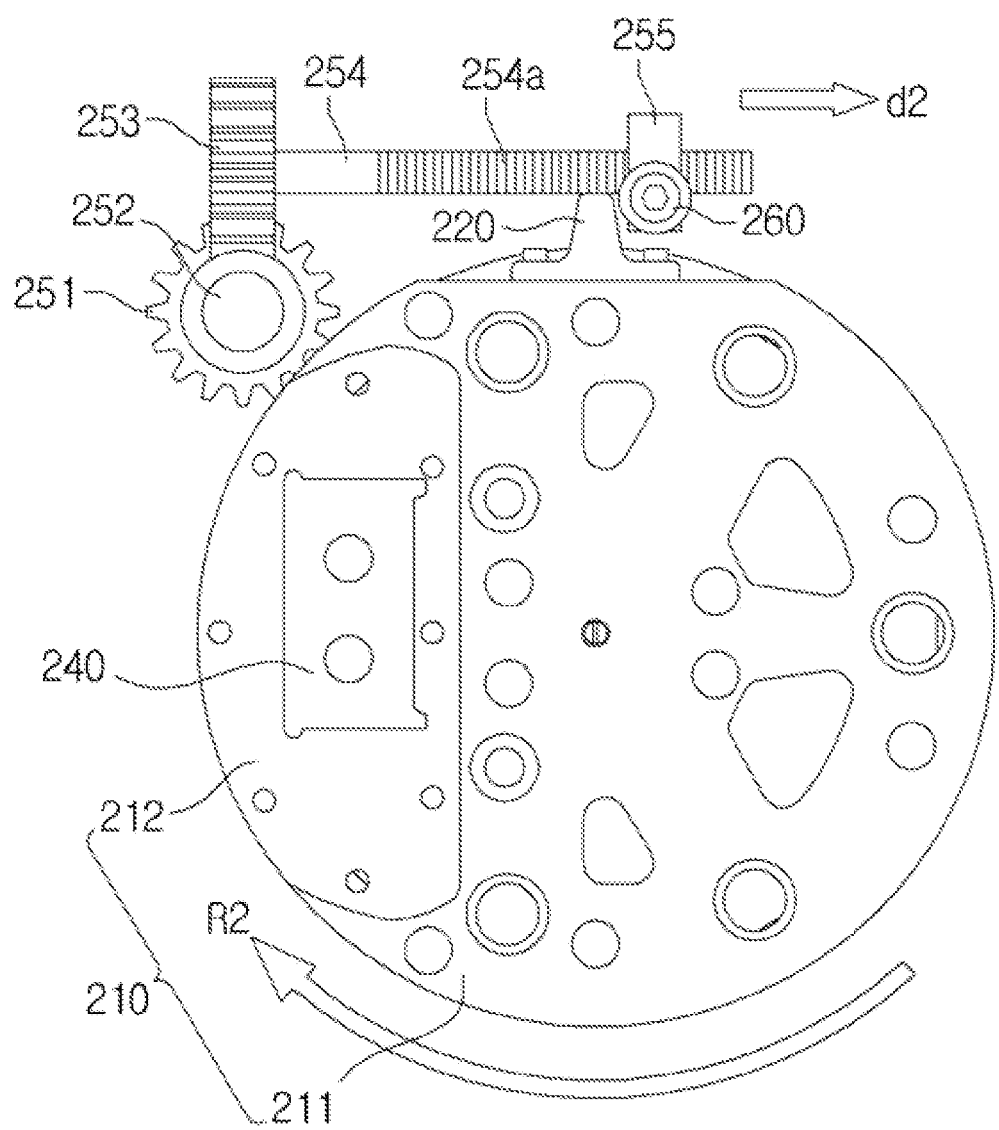

FIG. 10 and FIG. 11 are views illustrating a movement of the stopper according to a rotation of the rotating frame in accordance with another embodiment of the present disclosure.

As shown in FIG. 10 and FIG. 11, if the rotating frame 230 is rotated, the first gear 251 is rotated by a movement of the rotating frame 230, and the second gear 253 is rotated by a rotation of the first gear 251. Since the second shaft 254 coupled to the second gear 253 is rotated due to the rotation of the second gear 253, the housing 255 coupled to the second shaft 254 is also moved, thereby moving the stopper 260.

According to an embodiment of the present disclosure, if the rotating frame 230 is rotated in the counterclockwise direction R1, the stopper 260 may be moved from the first point to the second point in the first direction D1, and if the rotating frame 230 is rotated in the clockwise direction R2, the stopper 260 may be moved from the second point to the first point in the second direction D2. However, the present disclosure is not limited thereto, and a movement direction of the stopper 260 may be changed according to a spiral direction of the thread portion 254a formed on the second shaft 254.

The first gear 251 reduces the number of rotations of the second gear 253 as compared with a rotation of the rotating frame 230 to prevent the stopper 260 from being excessively moved. In addition, the second gear 253 can adjust a location of the stopper 260 according to a rotation of the first gear 251. Depending on a configuration of the first gear 251 and the second gear 253, it is possible to determine the movement degree of the stopper 260, which is caused by a movement of the rotating frame 230.

According to an embodiment of the present disclosure, it is possible to convert a rotary motion of the rotating frame 230 into a linear movement of the stopper 260. Since the stopper 260 is moved in a certain zone according to a movement of the rotating frame 230, in order for the protrusion 220 to be in contact with the stopper 260, the rotating frame 230 should be rotated 180° or more in one direction, so that it is possible to rotate 360° the X-ray-generating unit 70. Due to the above, it is possible to prevent a blind spot from being generated in which the X-ray-generating unit 70 cannot be rotated.

According to one aspect of the present disclosure, since the stopper securing the rotating frame of the rotating unit can be moved in the preset zone, it is possible to prevent a blind spot caused by a restriction of the rotation of the rotating frame from being generated.

Although the specific embodiments of the present disclosure have been shown and described, the present disclosure is not limited the above embodiments, it would be appreciated by those skilled in the art that changes may be made in these embodiments without departing from the principles and spirit of the disclosure, the scope of which is defined in the claims and their equivalents.

What is claimed is:

1. An X-ray image apparatus, comprising;
an X-ray-generating unit configured to generate X-rays and radiate the X-rays;
an X-ray-detecting unit configured to detect the X-rays radiated from the X-ray-generating unit; and
a rotating unit configured to rotate the X-ray-generating unit;
wherein the rotating unit comprises:
a rotating frame coupled to the X-ray-generating unit;
a protrusion coupled to the rotating frame to rotate with the rotating frame; and
a stopper disposed outside of the rotating frame and configured to make contact with the protrusion to stop a rotation of the rotating frame,
wherein the stopper is moved linearly in a preset zone to make contact with the protrusion.

2. The X-ray image apparatus according to claim 1, wherein the stopper is coupled to a driving unit for moving the stopper and the driving unit moves the stopper in a first direction when the rotating frame is rotated in a counterclockwise direction and moves the stopper in a second direction when the rotating frame is rotated in a clockwise direction.

3. The X-ray image apparatus according to claim 2, wherein the driving unit comprises at least one elastic member, and
the stopper is able to move in the preset zone by way of the elastic force of the at least one elastic member.

4. The X-ray image apparatus according to claim 3, further comprising a housing to which the at least one elastic member is coupled, the housing being configured to receive the stopper.

5. The X-ray image apparatus according to claim 4, wherein the at least one elastic member comprises a first elastic member coupled to one side of the housing and a second elastic member coupled to another side of the housing.

6. The X-ray image apparatus according to claim 4, further comprising a bracket to which the housing is coupled, the bracket comprising a groove for guiding a movement of the elastic member.

7. The X-ray image apparatus according to claim 2, wherein the driving unit comprises one or more gears.

8. The X-ray image apparatus according to claim 7, further comprising a housing coupled to the stopper via one side thereof and coupled to the gear via another side thereof.

9. The X-ray image apparatus according to claim 8, further comprising a shaft coupled to the gear via one side thereof and coupled to the housing via another side thereof.

10. The X-ray image apparatus according to claim 9, wherein the shaft has a thread portion provided on at least a portion thereof to allow the stopper to be moved along the thread portion.

11. The X-ray image apparatus according to claim 2, wherein the driving unit further comprises a power-generating device generating a power for moving the stopper.

12. The X-ray image apparatus according to claim 1, further comprising a buffer part coupled to the stopper for preventing generation of noise or damage caused by the stopper coming into contact with the protrusion.

13. An X-ray image apparatus, comprising;
an X-ray-generating unit configured to radiate X-rays;
an X-ray-detecting unit configured to detect the X-rays radiated from the X-ray-generating unit; and
a rotating unit configured to rotate at least one of the X-ray-generating unit and the X-ray detecting unit, wherein the rotating unit comprises:
a rotating frame coupled to at least one of the X-ray-generating unit and the X-ray detecting unit;
a stopper disposed outside of the rotating frame and configured to make contact with one side of the rotating frame to stop a rotation of the rotating frame; and
a driving unit for moving the stopper from a first point to a second point or from the second point to the first point, wherein the stopper is moved linearly from the first point to the second point or from the second point to the first point.

14. The X-ray image apparatus according to claim 13, further comprising a protrusion configured to protrude from the rotating frame to allow the stopper to come into contact with the protrusion to stop the rotation of the rotating frame.

15. The X-ray image apparatus according to claim 14, wherein the stopper comprises a head part and a body part extending from the head part, the head part being configured to come into contact with the protrusion.

16. The X-ray image apparatus according to claim 14, wherein the driving unit comprises at least one elastic member, and
the stopper is moved from the first point to the second point by a linear movement of the elastic member.

17. The X-ray image apparatus according to claim 16, wherein the elastic member comprises a first elastic member that is compressed when the stopper is moved to the second point and a second elastic member that is compressed when the stopper is moved to the first point.

18. The X-ray image apparatus according to claim 16, wherein the stopper further comprises a bracket provided for preventing the stopper from being deviated from a zone between the first point and the second point and a housing coupled to the bracket via one surface thereof and coupled to the stopper through another surface thereof.

19. The X-ray image apparatus according to claim 15, wherein the driving unit comprises at least one gear, and
the stopper is moved from the first point to the second point by a rotational movement of the gear.

20. The X-ray image apparatus according to claim 19, wherein the at least one gear comprises a first gear rotated according to a rotation of the rotating frame and a second gear determining a location of the stopper according to a rotation of the first gear.

21. A rotating unit configured to rotate an X-ray apparatus comprising one of an X-ray-generating unit and an X-ray-detecting unit, the rotating unit comprising:
a rotating frame coupled to the X-ray apparatus;
a protrusion coupled to the rotating frame to rotate with the rotating frame; and
an adjustable stopper disposed outside of the rotating frame and configured to make contact with the protrusion to stop a rotation of the rotating frame,
wherein the adjustable stopper is moved linearly in a preset zone to make contact with the protrusion.

* * * * *